United States Patent [19]

Maddox

[11] 4,019,364
[45] Apr. 26, 1977

[54] METHOD AND APPARATUS FOR TESTING WELDS BETWEEN DISSIMILAR METALS BY USING THE SEEBECK EFFECT

[75] Inventor: Harry L. Maddox, Reynoldsburgh, Ohio

[73] Assignee: Western Electric Company, Inc., New York, N.Y.

[22] Filed: Sept. 8, 1975

[21] Appl. No.: 610,964

[52] U.S. Cl. .......................... 73/15 FD; 73/359 R; 324/51; 340/253 W
[51] Int. Cl.² ................. G01N 25/72; G01R 31/00; G08B 21/00
[58] Field of Search ............ 73/15 R, 15 FD, 15.4, 73/359; 219/109, 110, 118, 121 LM; 324/32, 51; 340/228 R, 248 W, 253 W

[56] References Cited

UNITED STATES PATENTS

| | | | |
|---|---|---|---|
| 3,406,272 | 10/1968 | Ehrlich | 219/109 |
| 3,409,755 | 11/1968 | Munro | 219/110 |
| 3,756,067 | 9/1973 | Cushman | 73/15 |
| 3,821,562 | 6/1974 | Davis et al. | 73/359 |
| 3,829,849 | 8/1974 | Stauffer | 340/228 |
| 3,873,830 | 3/1975 | Foster | 73/15 |
| 3,930,159 | 12/1975 | Marquet | 73/359 |

OTHER PUBLICATIONS

Condra et al., "Thin Film Thermocouple" in Western Electric Technical Digest No. 32, 10/73.

Primary Examiner—Herbert Goldstein
Attorney, Agent, or Firm—K. R. Bergum; R. P. Miller

[57] ABSTRACT

To test certain structural characteristics of a weld formed between two dissimilar metals in order to test the quality, or structural integrity, of the weld, the emf generated at the weld bond interface during welding, as a result of the Seebeck effect (thermocouple), is monitored. As the weld cools, the emf decreases at a first essentially rapid rate with respect to time until the weld begins to recrystallize, or fuse, at which point the emf decreases at a second and slower rate since the latent heat of fusion of the metals decreases the cooling rate of the weld. When recrystallization is complete, the emf decreases at an essentially exponential rate. It has been discovered the rate of change of the emf with respect to time during recrystallization is an indication of the quantity of the metal involved in the weld where the weld is exposed to a constant heat sink, such as the atmosphere, since the more metal that is involved in the weld the slower the weld will cool during fusion, and vice versa. The quantity of metal involved in the weld is indicative of the quality, or structural integrity, of the weld, since the more metal that is involved in the weld the greater the likelihood that a secure weld has been formed. The rate of change of the emf with respect to time during fusion is compared with a predetermined rate of emf change with respect to time which is indicative of a predetermined weld mass of the metals to obtain one indication of the quality of the weld. Further, the occurrence of any discontinuity in the emf during cooling of the weld is detected, and indicates the development of a crack or a venting gas bubble at the weld bond interface, either of which decreases the integrity of the weld.

6 Claims, 4 Drawing Figures

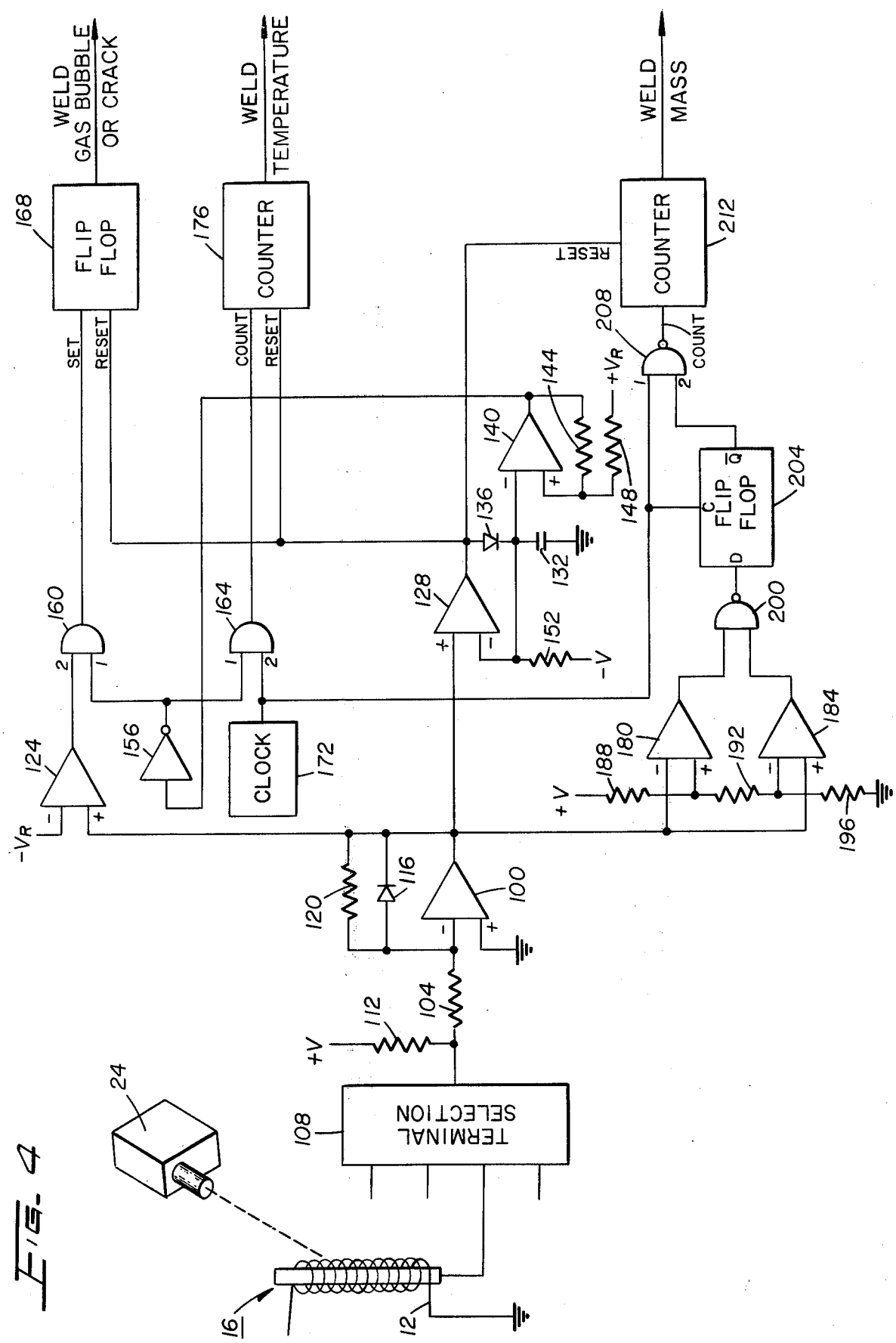

METHOD AND APPARATUS FOR TESTING WELDS BETWEEN DISSIMILAR METALS BY USING THE SEEBECK EFFECT

BACKGROUND OF THE INVENTION

1. Field of the Invention

The present invention relates to methods of and apparatus for testing welds, and in particular to a method of and apparatus for determining the structural integrity of a weld between dissimilar metals by monitoring the emf generated at the juncture between the metals during the formation of the weld.

2. Description of the Prior Art

In the manufacture of electronic circuits, joining conductors of electricity by welding presents the problem of testing the mechanical integrity, or quality, of the weld in a nondestructive manner. Mechanical tests are often impractical because they are time consuming and can reduce the quality of the weld, or become destructive tests unless precisely controlled.

To avoid the possibility of degrading or destroying a weld between electrical conductors with a mechanical testing apparatus, various electrical testing techniques have been developed. One technique involves passing current through the weld while measuring the voltage thereacross, and then comparing the measured voltage with a voltage measured across a section of conductor without a weld when a similar magnitude current is passed therethrough. A disadvantage of this technique is the difficulty of coupling a high current to the weld while measuring a low voltage thereacross, and then comparing the two independent voltage measurements.

Another technique is to use a Kelvin bridge to measure the resistance of a length of conductor which includes the weld, which resistance is then compared with the resistance of a similar length of conductor which does not include a weld. A disadvantage of this technique is the inconvenient and time consuming operation of adjusting the Kelvin bridge for each resistance measurement. A variation of this technique is to measure the resistance across a weld while the weld is subjected to a cyclically varying pressure, it being assumed that a weld having a high degree of mechanical integrity will exhibit minimal changes in resistance in response to pressure, while a weld having less mechanical integrity will exhibit significant resistance changes in response to pressure. However, this technique requires bulky equipment for exerting pressure on the weld, and similarly requires the time consuming operation of adjusting a Kelvin bridge for each resistance measurement.

To overcome the aforementioned disadvantages in testing welds between conductors in electronic circuits, another method of testing a weld involves employing conductors of dissimilar metals and measuring the maximum emf generated across the weld bond interface during the welding operation as a result of the Seeback effect (thermocouple). The magnitude of the generated emf is directly related to the temperature of the weld bond interface, and the maximum emf measured is therefore representative of the maximum temperature reached at the weld bond interface and allows a determination to be made whether or not a temperature sufficient to effect a weld is reached. While this technique is particularly useful in ascertaining whether or not a temperature sufficient to effect a weld is reached, it does not allow a determination of the quality of the resulting weld. That is, no indication is provided as to the mass of the weld, or whether cracking or gas venting has occurred at the weld bond interface during the formation of the weld, all of which affect the mechanical integrity of the weld.

SUMMARY OF THE INVENTION

In accordance with the present invention, a weld formed between two dissimilar metals by the application of welding energy to the weld, where an emf is generated across the weld bond interface and has a value directly related to the temperature of the weld interface as a result of the Seebeck effect, is tested to determine the mass of the weld and to detect whether any cracks have occured through the weld during the formation of the weld. In determining the mass of the weld, the emf generated across the weld bond interface as a result of the Seebeck effect is monitored, and the rate of change of the monitored emf with respect to time is detected subsequent to the application of the welding energy to the weld. The detected rate of change of the monitored emf with respect to time is then compared with a predetermined rate of emf change with respect to time which is indicative of a predetermined weld mass of the metals. In detecting occurrence of a crack through the weld, the emf across the weld as a result of the emf generated across the weld bond interface is monitored, and the occurrence of a loss of the monitored emf subsequent to the application of the welding energy to the weld is detected. If a loss is detected, an indication thereof is generated.

Preferably, the mass of the weld material is compared with a predetermined weld mass by amplifying the emf generated across the weld bond interface, and by generating first and second reference voltages, the value of the first reference voltage equaling the value of the amplified emf when the temperature of the weld bond interface is at the temperature where recrystallization of the weld has essentially begun, and the value of the second reference voltage equaling the value of the amplified emf when the temperature of the weld bond interface is at the temperature where recrystallization of the weld is essentially complete. Clock pulses are generated at a known frequency, the value of the amplified emf is compared with the values of the first and second reference voltages, and the number of clock pulses which occur during the time that the amplified emf has a value within the range of values defined by the first and second reference voltages, as the weld cools subsequent to the application of the heating energy thereto, are counted. The counted number of clock pulses is then compared with a predetermined minimum number of clock pulses which would occur while the value of the amplified emf is within the range of values defined by the first and the second reference voltages if the mass of the weld is equal to a predetermined minimum mass, and an indication is generated of a counted number of clock pulses which is less than the predetermined minimum number of clock pulses.

In detecting the occurrence of a crack through the weld where the emf across the weld is monitored, the point is detected when the monitored emf stops increasing in a first direction, as the weld is heated upon the application of the welding energy thereto, and increases in a second and opposite direction, as the weld cools subsequent to the application of the welding energy thereto. The occurrence of a loss of the monitored emf, upon the emf increasing in the second direction, is then detected and an indication is generated thereof.

Other advantages and features of the invention will be apparent upon consideration of the following detailed description when taken in conjunction with the appended drawings.

BRIEF DESCRIPTION OF THE DRAWINGS

FIG. 4 is a circuit for monitoring the emf developed between the wire and the terminal of FIG. 1 during the welding thereof, and for generating an indication of structural integrity of the weld effected therebetween in accordance with the teachings of the present invention.

DETAILED DESCRIPTION

Figure 1:
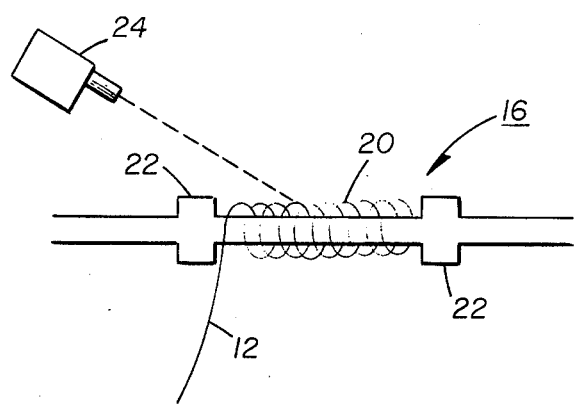
FIG. 1 illustrates a wire wound around a terminal and being welded thereto with a beam from a laser.

The drawings illustrate a system for nondestructively determining, or testing, certain structural characteristics of a weld effected between two articles of dissimilar metals to test the quality or structural integrity of the weld. In a contemplated use of the invention, and as shown in FIG. 1, the articles are a Cu wire 12 and a Monel terminal 16 (approximately 80% Ni and 20% Cu). The wire 12 is wrapped around a center portion 20 of the terminal 16 between a pair of locating ears 22, and is to be welded thereto by welding energy, such as by the energy in a beam from a laser 24. Since the wire 12 and the terminal 16 are of dissimilar metals, a small voltage, or emf, is generated when an interface, such as a weld bond interface, is formed therebetween, which voltage is proportional to the temperature of the interface as a result of the Seebeck effect (thermocouple). The emf may be detected across the weld and monitored during welding by any appropriate circuitry, such as that shown in FIG. 4 or by, for example, an oscilloscope. It is to be understood that while the invention will be described in terms of testing the quality of a weld between a wire and a terminal of dissimilar metals, the teachings of the invention are intended to include, and may be applied to, the testing of the quality of a weld effected between any two articles of dissimilar metal.

Figure 2:
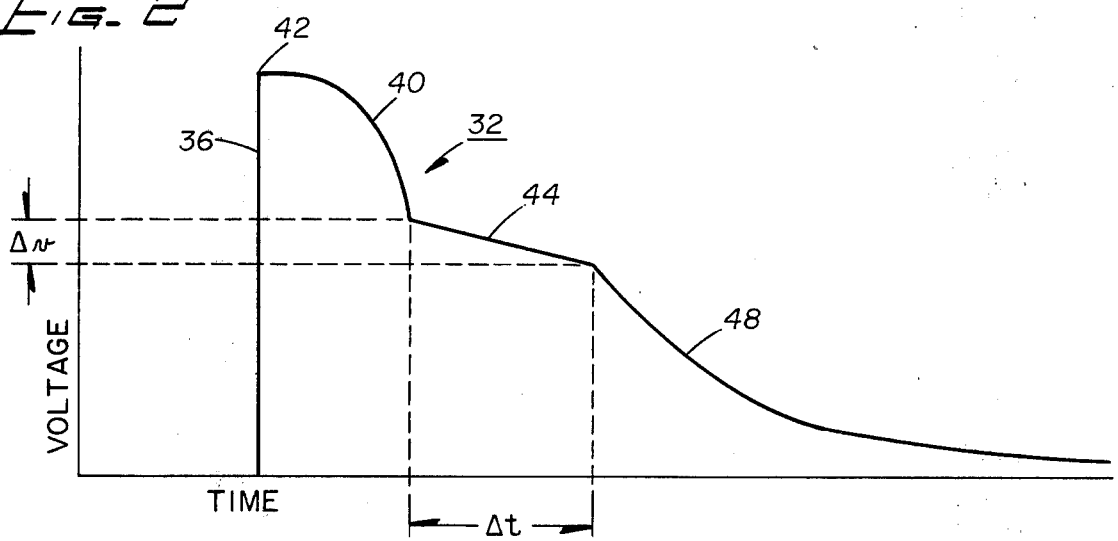
FIG. 2 illustrates a curve of the emf developed with respect to time between the wire and the terminal of FIG. 1 during welding, where the wire and the terminal are of dissimilar metals and the wire is initially coated with a vaporizable, electrically insulating coating.

The wire 12 may or may not initially have a vaporizable, insulating coating thereon, such as varnish. In the event that the wire 12 does have a varnish coating thereon, no electrical connection initially exists between the wire 12 and the terminal 16. However, during welding the energy in the beam from the laser 24 vaporizes the varnish coating on the wire 12 in the weld area and an electrical connection is established between the wire and the terminal. FIG. 2 illustrates a curve 32 of the emf generated across the weld bond interface, or the junction area, between the wire 12 and the terminal 16 when there is initially no electrical connection between the wire and the terminal, and where the terminal has a vaporizable insulating coating thereon. As the wire 12 and the terminal 16 are heated by the beam from the laser 24, a point is reached whereat the insulation on the wire 12 vaporizes and a molten juncture is rapidly formed between the Cu wire 12 and the Monel terminal 16 in the weld area. This establishes an electrical connection between the wire and terminal, and the emf across the interface therebetween increases rapidly, as shown by a portion 36 of the curve 32. The magnitude of the emf is, of course, directly related to the temperature of the interface between the wire and the terminal.

When power to the laser 24 is shut off after the weld area of the wire 12 and the terminal 16 has reached a molten and sufficiently high temperature state, the weld begins to cool upon exposure to the terminal and wire mterial outside of the weld area and the emf between the wire 12 and the terminal 16 decreases at a first essentially rapid rate, shown by a portion 40 of the curve 32, from a peak value representative of the maximum temperature reached by the weld bond interface, shown at a point 42 of the curve 32. This continues until the molten and alloyed metals of the wire 12 and the terminal 16 begin to fuse, or recrystallize, to form the weld, at which point the emf across the weld bond interface decreases at a second and slower rate, as shown by a portion 44 of the curve 32, since during recrystallization of the weld the latent heat of fusion of the metals decreases the cooling rate thereof. After recrystallization of the weld is complete, the emf across the weld bond interface decreases at an essentially exponential rate, as shown by a portion 48 of the curve 32, as the weld continues to cool.

The mass of the weld material is an indication of the quality or structural integrity of the weld, since the greater the mass of the weld material the greater the probability that the resulting weld will have structural strength, and the less the mass of the weld material the less the probability that the resulting weld will have structural strength. Since the mass of the weld material, for a given or constant weld heat sink, determines the rate at which the weld cools, the greater the mass of the weld material the slower the weld junction cools from a first predetermined high temperature to a second and lower predetermined temperature, and the less the mass of the weld material the more rapidly the weld junction cools from the first to the second predetermined temperatures. Therefore, by measuring the time required for the weld junction to cool from a selected first to a selected second predetermined temperature, an indication of the mass of the weld material, or of the quantity of material involved in the weld, is obtained. If the first temperature is selected to be above the temperature at which the weld begins to recrystallize, or fuse, at which temperatures the mass of the weld continues to change as more molten material is added thereto, a correlation between the cooling rate of the weld and the mass thereof is difficult to obtain. If the first temperature is selected to be below the temperature at which recrystallization of the weld is complete, the change in temperature of the weld with respect to time is increasingly subject to external influences, such as the heat sink effect of the surrounding atmosphere, making a correlation between the cooling rate of the weld and the mass thereof difficult to obtain. However, if the first predetermined temperature is at the temperature where weld recrystallization has just begun, and if the second and lower predetermined temperature is at the temperature where weld recrystallization has essentially been completed, the weld has a final, indirectly determinable mass, as the cooling rate thereof is essentially subject to the constant heat sink effect of the remaining material of the wire and the terminal, and an accurate measurement of the rate of change of temperature of the weld junction with respect to time can be made. That is, to obtain an accurate indication of the mass of the weld, or of the quantity of material involved in the weld, the rate of change in temperature of the weld with respect to time is preferably measured through recrystallization of the weld.

Since the emf developed across the weld bond interface between the wire 12 and the terminal 16 is proportional to, or directly related to, the temperature of the weld bond interface, the slope of the emf curve 32 along the portion 44 thereof, or the change in emf with respect to time ($\Delta v/\Delta t$) during the time when the molten and alloyed metals are recrystallizing to form the weld, is an indication of the rate with respect to time at which the weld material is cooling, and is therefore an indication of the mass of the weld material and of the structural strength of the resulting weld. Therefore, by using appropriate circuitry to determine the slope, or the rate of change of emf with respect to time, of the portion 44 of the curve 32, such as the circuitry shown in FIG. 4, an indication of the mass of the resulting weld is obtained.

Figure 3:
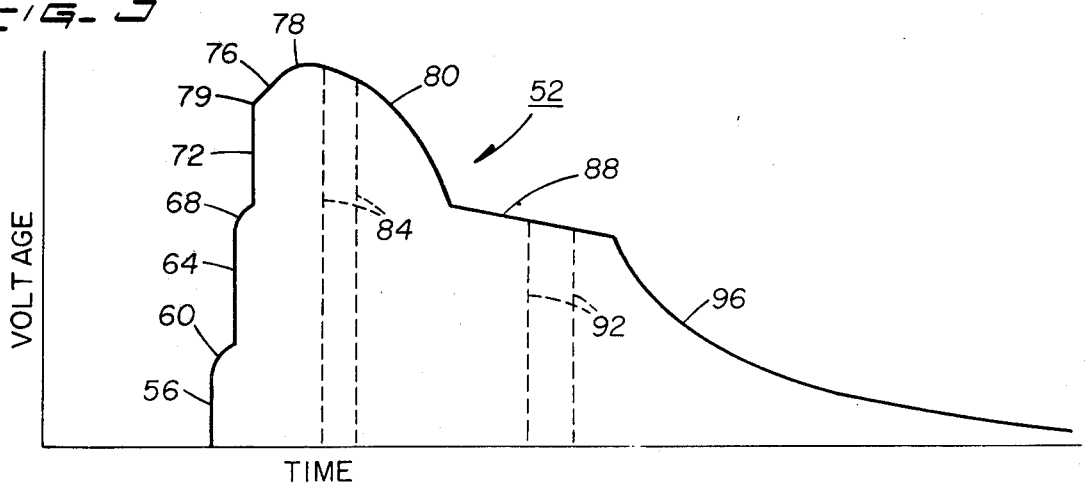
FIG. 3 shows a curve of the emf developed with respect to time between the wire and the terminal of FIG. 1 during welding, where the wire and the terminal are of dissimilar metals and are initially in electrical contact only in the weld area.

If the wire 12 is uninsulated, and an electrical connection initially exists between the wire and the terminal 16 only in the weld area, the curve of the emf generated across the interface between the wire and the terminal during the welding together thereof may be interpreted, if desired, to obtain additional information about the various temperature states of the weld material during the heating thereof. For example, FIG. 3 shows a curve 52 of the emf generated across the weld bond interface of an uninsulated wire 12 and the terminal 16, where an electrical connection initially exists only in the weld area between the wire and the terminal prior to the heating and welding thereof. The main difference between the emf curves 32 and 52 is that in the curve 32 the wire 12 and the terminal 16 are in a high temperature state at the time the vaporizable insulation on the wire vaporizes to establish an electrical connection between the wire and the terminal in the weld area, so that the rate of emf increase across the weld bond interface is rapid, whereas in the curve 52 an electrical connection exists between the wire and the terminal prior to the heating thereof, so that the emf increase across the weld bond interface is representative of the various temperature states of the wire and the terminal junction. It should be noted that if a connection exists between the wire and the terminal at a point other than at the weld area, the emf generated across the weld bond interface will be shorted out.

Referring to FIG. 3, when the wire 12 and the terminal 16 begin to heat at their interface, or juncture, the emf thereacross increases rapidly, as shown by a portion 56 of the curve 52. The Cu wire 12 has a lower melting point than the Monel terminal 16, and while the wire 12 melts, as shown by a sloping portion 60 of the curve 52, the rate of heating of the interface between the wire and the terminal decreases as result of the latent heat of fusion of the wire 12 in the weld area. When the Cu wire has been melted, the temperature of the interface between the wire and the terminal 16 again increases at a more rapid rate, as shown by a portion 64 of the curve 52, until the melting point of the Monel terminal 16 is reached. Then, while the terminal 16 melts, the rate of heating of the interface between the wire 12 and the terminal 16 decreases, as shown by a portion 68 of the curve 52, as a result of the latent heat of fusion of the terminal 16 in the weld area. After the terminal 16 has melted, the temperature of the interface between the wire 12 and the terminal 16 again increases at a more rapid rate, as shown by a portion 72 of the curve 52.

Ideally, power to the laser 24 is turned off after a temperature has been reached by the weld material which is sufficiently high to ensure that a weld can be formed and before the temperature of the weld material reaches the vaporization temperature of Cu to prevent boiling of the Cu in the weld with a resulting decrease in material for forming the weld or, in the alternative, to prevent the Cu from being completely boiled away with the result that insufficient weld material is available to form a weld. The point at which the temperature of the weld material becomes sufficient to vaporize the Cu is indicated by a portion 76 of the emf curve 52, where the rate of heating of the weld material, and therefore of the weld bond interface between the wire 12 and the terminal 16, again decreases as a result of the latent heat of vaporization of the Cu in the weld. To ensure that the weld material has been heated to a temperature which is sufficiently high to form a secure weld, and to avoid vaporization of the Cu, the circuit of FIG. 4 detects the maximum value of the emf curve 52, as shown at a point 78, to determine whether the maximum temperature reached by the weld is both sufficient to form a secure weld and below the vaporization temperature of Cu, as shown by the point 79 of the curve 52. It is understood that a sloping portion, similar to the portion 76 of the curve 52, would occur in the emf curve 32 where the wire is coated with a vaporizable insulation if the temperature of vaporization of Cu were reached by the weld material, since by that point the insulation on the wire 12 would have been vaporized and an electrical interface would have been established between the wire and the terminal 16.

When power to the laser 24 is turned off the temperature of the weld bond interface between the wire 12 and the terminal 16 decreases at a first essentially rapid rate, as shown by a portion 80 of the emf curve 52, where the weld mass transfers heat to its heat sink, which is essentially the remaining material of the wire and terminal not involved in the weld. During this time, the occurrence of a harmful gas bubble in the weld which passes completely across the weld is evidenced by a discontinuity in the curve 52, or by a loss of the Seebeck voltage measured across the weld, such as shown by a dotted portion 84 of the curve 52 as a result of a momentary loss of continuity through the weld. While a momentary loss in continuity is illustrated by the portion 84 of the curve 52, it is understood that venting of a gas bubble could also readily result in a permanent loss in continuity through the weld. A gas bubble through the weld ordinarily results in a physical break through the weld and impairs the structural integrity or quality of the weld, and should a discontinuity such as the discontinuity 84 occur it is detected by the circuit of FIG. 4.

While the weld materials recrystallize to form the weld, the temperature of the weld bond interface and therefore of the emf curve 52 decreases at a second and slower rate, shown at a portion 88 thereof which is similar to the portion 44 of the curve 32, as a result of the latent heat of fusion of the weld materials. Since, as stated, the mass of the weld materials determines, for a constant heat sink, the cooling rate of the weld, the rate of change of emf of the portion 88 of the curve 52 with respect to time is an indication of the mass of the weld material, and therefore of the integrity of the weld. A discontinuity in the curve 52 which occurs during the portion 88 thereof, such as the momentary discontinuity shown by the dotted portion 92 as a result of a momentary loss of continuity through the weld bond interface, indicates that a crack, or break, has developed through the weld during recrystallization of the weld, and that the opposing faces of the crack have come into contact with each other to reestablish continuity through the weld, which crack or break impairs the integrity of the weld and renders the weld unacceptable. It is understood that a crack through the weld could just as readily result in a permanent loss in the Seebeck voltage measured across the weld, the momentary discontinuity 92 only being shown for the purpose of illustration. Such discontinuity 92 is detected by the circuit of FIG. 4. After fusion of the weld material is complete, the curve 52 decreases at an essentially exponential rate, as shown by a portion 96 thereof which is similar to the portion 48 of the curve 32, as the weld material cools at an essentially exponential rate.

Referring now to the circuit of FIG. 4, to test the quality, or integrity, of a weld between a wire 12 and a terminal 16, the wire 12 is connected to a reference potential, such as ground, and the terminal 16 is electrically connected to the inverting input of an operational amplifier (op amp) 100 through a resistor 104, the noninverting input of which is connected to ground potential. While only one terminal 16 wrapped with a wire 12 is shown, where more than one terminal wrapped with a wire to be welded thereto is to be tested a terminal selection gate 108 selectively connects one terminal at a time to the op amp 100. As will be seen, when the laser 24 is energized to weld the wire 12 to the terminal 16 the circuit indicates that (1) continuity has been established between the wire and the terminal, (2) the weld junction temperature has exceeded the melting points of both the wire and the terminal materials and has not exceeded the boiling point of either material, (3) continuity has not been momentarily or permanently lost through the weld during the cooling of the weld, and (4) the mass of the weld material is in excess of a predetermined minimum mass. Continuity interruptions can occur when gas bubbles vent or when cracking occurs through the weld.

If the wire 12 is coated with a heat vaporizable insulation, before continuity is established between the wire and the terminal 16 current through a resistor 112 and the resistor 104 from a positive source of voltage (not shown) to the inverting input of the op amp 100 causes the op amp 100 to provide feedback through a diode 116 to reduce the gain of the op amp 100. This prevents amplification of noise signals that might be picked up by the floating connection to the terminal 16. When continuity is established at the weld junction area between the wire 12 and the terminal 16, as occurs upon vaporization of the insulation during the welding cycle, current through the resistor 112 flows through, and produces only a negligible voltage drop across, the low resistance of the connection between the wire 12 and the terminal 16, and the op amp 100 reverts to a high gain mode determined by the ratio of the resistor 104 to a resistor 120. The Seebeck voltage for a Cu wire 12 and a Monel terminal 16, where the Cu wire 12 is grounded, increases in the negative direction for increasing temperatures. This Seebeck voltage is measured across the weld and is, as shown, applied to the inverting input of the op amp 100, and therefore the output of the op amp 100 is positive going in response to the Seebeck voltage.

The output of the op amp 100 is applied to a noninverting input to an op amp 124, the inverting input of which is connected to a regulated source of negative voltage (not shown), and to a noninverting input to an op amp 128. The outputs of the op amps 124 and 128 are therefore positive going in response to a positive going output from the op amp 100. The output from the op amp 128 charges a capacitor 132 through a diode 136 to a peak voltage representing the peak temperature reached by the junction between the wire 12 and the terminal 16 during the heating thereof, and the voltage across the capacitor 132 is applied to an inverting input to the op amp 128, so that the output of the op amp 128 goes negative after the peak Seebeck voltage has been passed at the end of the heating cycle when the voltage at the non-inverting input to the op amp goes in a negative direction. A negative going transition at the output of the op amp 128 therefore indicates when weld junction cooling starts.

The voltage across the capacitor 132 is also applied to an inverting input to an op amp 140, the output of which is connected to a regulated source of positive voltage (not shown) through a resistor 144 and a resistor 148. The noninverting input to the op amp 140 is connected to the juncture between the resistors 144 and 148. As the weld junction temperature increases during heating and the op amp 128 charges the capacitor 132 to a peak voltage representing the peak temperature reached by the weld junction, the output of the op amp 140 goes negative when the capacitor 132 is charged to a voltage more positive than, or beyond, a reference voltage determined by the voltage at the juncture between the resistors 144 and 148, which reference voltage is selected to be equal to the voltage at the output of the op amp 128 when the temperature of the weld bond interface is equal to the temperature at which weld recrystallization has just been completed. Then, when weld heating stops and the weld starts to cool the output of the op amp 128 goes negative, the diode 136 is reverse biased, the capacitor 132 discharges through a resistor 152, and the output of the op amp 140 goes positive when the voltage across the capacitor 132 decreases and becomes less positive than the reference voltage at the juncture between the resistors 144 and 148. Therefore, the output of the op amp 140 is negative whenever the capacitor is charged to a voltage more positive than the the reference voltage, or whenever the weld junction temperature is in excess of a predetermined minimum temperature, and is negative at other times.

The output from the op amp 140 is applied through an inverting amplifier 156 to a first output of an AND gate 160 and to a first input of an AND gate 164. This enables the AND gates 160 and 164 to pass signals at second inputs thereto to the outputs thereof whenever the voltage across the capacitor 132 is greater than the reference voltage, or whenever the weld junction temperature is greater than the predetermined minimum temperature, and inhibits the AND gates 160 and 164 from passing signals at the second inputs thereto to the outputs thereof whenever the voltage across the capacitor 132 is less than the reference voltage, or whenever the weld junction temperature is less than the predetermined minimum temperature.

DETECTING CONTINUITY GAS BUBBLES AND CRACKS

Cracks and gas bubbles which occur through the weld cause a momentary or permanent loss in continuity through the weld and are evidenced by discontinuities in the Seebeck voltage measured across the weld. During heating of the weld material by the laser 24, gas bubbles commonly occur in the weld as a result of the roiling nature of the weld material, which gas bubbles do not affect the structural integrity of the resulting weld. After recrystallization of the weld is complete, gas bubbles and cracks no longer occur. However, from the time that the weld begins to cool until the time that recrystallization of the weld material is essentially complete, a gas bubble or crack which occurs through the weld affects the structural integrity, or quality of the weld, and renders the weld unacceptable. To detect such gas bubbles and cracks, the output of the op amp 124 is applied to the second input to the AND gate 160, and the output of the AND gate 160 is applied to a set input to a flip flop 168. The output from the op amp 128 is applied to a reset input to the flip flop 168 to hold the flip flop 168 in a reset state when the output of the op amp 128 is positive, and to enable the flip flop 168 to be set when the output of the op amp 128 is negative. Therefore, the flip flop 168 is enabled to be set after the heating cycle of the weld terminates and weld cooling begins, and the AND gate 160 is enabled to pass a signal from the op amp 124 to the set input of the flip flop 168 during the time that the voltage across the capacitor 132 is above the reference voltage, with the result that the flip flop 168 is enabled to be set by a signal from the op amp 124 which occurs from the time that the weld junction begins to cool until the time that the weld junction has cooled to the predetermined minimum temperature, which predetermined minimum temperature is the temperature of the weld when recrystallization thereof is essentially complete.

As previously stated, a loss of continuity through the weld during cooling of the weld, as a result of a gas bubble or crack occurring through the weld, results in a loss or discontinuity in the Seebeck voltage measured across the weld, such as shown by the momentary discontinuities 84 and 92 of FIG. 3. With such a loss in continuity through the weld, a significant voltage drop is generated across the weld by the positive source of voltage through the resistor 112, and is applied to the inverting input to the op amp 100 to generate a negative voltage at the output of the op amp 100. This negative voltage is applied through the op amp 124 to the second input of the AND gate 160, and is enabled to pass through the AND gate 160 to the set input of the flip flop 180 to generate an output therefrom only during the period commencing with the start of weld cooling and terminating upon the voltage across the capacitor 132 becoming less than the reference voltage, which reference voltage occurs after recrystallization of the weld material is essentially complete. The output from the flip flop 168 is applied to any appropriate device (not shown) for indicating the occurrence of a gas bubble or a crack through the weld. It should again be noted that by holding the flip flop 168 reset until the heating cycle is completed and weld cooling commences, phenomena causing discontinuities through the weld during the heating cycle, which discontinuities during heating are not detrimental to the quality of the weld, do not cause an indication to be generated that the weld lacks quality. It should also be noted that should continuity not be established between the wire 12 and the terminal 16 during welding, the op amp 100 maintains a negative voltage at its output which is applied through the op amp 124 and the AND gate 160 to the flip flop 168 when weld cooling begins, to set the flip flop 168 to indicate that continuity does not exist.

DETERMINING THE MAXIMUM TEMPERATURE OF WELD

To determine both whether the weld material has reached a sufficiently high temperature to ensure that a structurally sound weld can occur, as well as whether the weld material has reached a temperature whereat the material thereof begins to vaporize, the output of a continuously running, known frequency clock 172 is applied to the second input of the AND gate 164, the output of which is applied to a count input of a counter 176. The output of the op amp 128 is applied to a reset input of the counter 176 to hold the counter reset when the output is positive, and to enable the counter to store a count therewithin when the output is negative. Therefore, the counter 176 receives a count from the clock 172 from the time that weld cooling begins, when the output from the op amp 128 goes negative, until the voltage across the capacitor 132 decreases to the reference voltage, at which point the output of the op amp 140 goes positive to disable, through the amplifier 156, the AND gate 164 from passing the clock pulses to the counter 176. For predetermined values of the capacitor 132 and the resistor 152, the time required for the capacitor 132 to discharge through the resistor 152 from a peak voltage representing the maximum weld junction temperature to the reference voltage is a function of the magnitude of the peak voltage, and therefore of the maximum temperature reached by the weld bond interface. Since the rate of the clock 172 is known, the number of clock pulses stored by the counter 176 from the time that cooling of the weld begins, and until the time that the voltage across the capacitor 132 decreases to the reference voltage, is an indication of the maximum temperature reached by the weld bond interface. Should the count in the counter 176 be less than a predetermined minimum count, which predetermined minimum count is representative of the count that would be reached if the temperature at the weld bond interface were at the minimum temperature required to effect a secure weld, an output is generated by the counter 176 to indicate that the temperature of the weld was less than that required to ensure that a secure weld resulted. Similarly, should the count in the counter 176 be greater than a predetermined maximum count, which predetermined maximum count is representative of the count that would be reached if the temperature at the weld bond interface reached the temperature at which weld material begins to vaporize, an output is generated by the counter 176 to indicate that the temperature of the weld is beyond the vaporization temperature of the weld material. Either indication denotes that the quality of the weld has been affected.

DETERMINING THE MASS OF THE WELD

As previously stated, the mass of the weld material is an indication of the structural integrity of the weld, since the greater the mass of the weld material the greater the probability that a structurally secure weld has resulted, and the less the mass of the weld material, the less the probability that a structurally secure weld has resulted. Also, the greater the mass of the weld material the more slowly the weld cools during recrystallization, or fusion when exposed to a constant heat sink of the remaining wire and terminal material not involved in the weld, and the less the mass of the weld the more rapidly the weld cools during fusion. To determine whether the mass of the weld is at least equal to a predetermined minimum weld mass, which predetermined minimum weld mass is sufficient to ensure that a secure weld has resulted, the output from the op amp 100 also is applid to an inverting input to an op amp 180 and to a noninverting input to an op amp 184. Three resistors 188, 192 and 196 are connected in series as a voltage divider between the positive source of potential and circuit ground, and the noninverting input of the op amp 180 is connected to the juncture between the resistors 188 and 192, and the inverting input of the op amp 184 is connected to the juncture between the resistors 192 and 196.

The values of the resistors 188, 192 and 196 are chosen, for a Cu wire and a Monel terminal, to apply a voltage to the noninverting input to the op amp 180 which is equal to the voltage at the output of the op amp 100 when the weld bond interface temperature is at a first predetermined high temperature which is essentially equal to the temperature at which the weld begins to fuse, or recrystallize, and to apply a voltage to the inverting input to the op amp 184 which is equal to the voltage at the output of the op amp 100 when the weld bond interface temperature is at a second and lower predetermind temperature which is essentially equal to the temperature at which recrystallization of the weld is complete. The outputs of the op amps 180 and 184 are applied to the inputs of a NAND gate 200, the output of which is applied to a data input of a flip flop 204. The clock 172 is applied to a clock input to the flip flop 204 as well as to a first input to a NAND gate 208, and the inverted output of the flip flop 204 is applied to a second input to the NAND gate 208. The output of the NAND gate 208 is applied to the count of a counter 212 which receives at a reset input thereto the output from the op amp 128.

The counter 212 is enabled by a negative voltage at its reset input to store a count applied to its count input, and therefore is enabled to store a count applied to its count input whenever the output of the op amp 128 becomes negative, which occurs when the weld begins to cool. The op amps 180 and 184, and the NAND gate 200, are arranged to apply a low voltage to the data input of the flip flop 204 whenever the temperature of the weld is within the temperature window defined by the voltage divider resistors 188, 192 and 196. With a low voltage at its data input the flip flop 204 generates, in response to a clock pulse at its clock input, a high voltage at its output which is applied to the second input to the NAND gate 208 to enable the NAND gate to pass therethrough, and to the counter 212, pulses from the clock 172. In this manner, the counter 212 stores therewithin the clock pulses generated by the clock 172 during weld cooling from a time when recrystallization of the weld material has essentially begun until a time when recrystallization of the weld material is essentially complete.

When the weld bond interface has cooled to the second predetermined temperature, or the temperature at which recrystallization of the weld material is essentially complete, the output of the NAND gate 200 goes high, the output of the flip flop 204 goes low with the next clock pulse applied to the clock input thereof, and the NAND gate 208 no longer passes to the counter 212 pulses from the clock 172. Since the rate of the clock 172 is known, the count stored within the counter 212 is representative of the time required for the weld material to recrystallize, which in turn is representative of the mass of the weld material. In other words, the count in the counter 172 is an indication of the slope, or of the rate of change of the Seebeck voltage with respect to time, during recrystallization of the weld material. If the count stored within the counter 212 is less than a predetermined count, which predetermined count is representative of a minimum mass of weld material required to ensure that a secure weld has resulted, an output is generated by the counter 212 to indicate that the mass of the weld is insufficient for the weld to have structural integrity, or strength. Again, it should be noted that the rate of change of the Seebeck voltage, or weld junction temperature with respect to time, is preferably made during recrystallization of the weld when the weld has a fixed mass, since when the temperature of the weld is above the recrystallization temperature thereof the weld mass changes as material is added thereto, and when the temperature of the weld is below the recrystallization temperature thereof the temperature changes in the weld are increasingly subject to external influences.

While one particular embodiment of the invention has been described in detail, it is understood that various other modifications and embodiments may be devised by one skilled in the art without departing from the spirit and scope of the invention.

What is claimed is:

1. In a method of testing a weld formed between two dissimilar metals by the application of welding energy to the weld, where an emf is generated across the weld bond interface and has a value related to the temperature of the weld bond interface as a result of the Seebeck effect:
    monitoring the emf across the weld as a result of the emf generated across the weld bond interface;
    detecting the occurrence of a loss of the monitored emf subsequent to the application of the welding energy to the weld and during the cooling thereof, and
    generating an indication of a detected loss of the monitored emf.

2. In a method of testing a weld as set forth in claim 1, the detecting step includes detecting the occurrence of a loss of the monitored emf across the weld from the time that the weld begins to cool and until recrystallization of the weld is essentially complete.

3. In a method of detecting the occurrence of a crack through a weld formed between two dissimilar metals by the application of welding energy to the weld, where an emf is generated across the weld bond interface and has a value directly related to the temperature of the weld bond interface as a result of the Seebeck effect:
    monitoring the emf across the weld as a result of the emf generated across the weld bond interface;

detecting when the monitored emf stops increasing in a first direction as the weld is heated upon the application of the welding energy thereto, and increases in a second and opposite direction as the weld cools subsequent to the application of the welding energy thereto;

detecting, upon the monitored emf increasing in the second direction, the occurrence of a loss of the monitored emf, and generating an indication of a detected loss of the monitored emf.

4. In a method of testing a weld formed between two dissimilar metals by the application of welding energy to the weld, where an emf is generated across the weld bond interface as a result of the Seebeck effect and has a value directly related to the temperature of the weld bond interface:

monitoring the value of the emf across the weld as a result of the emf generated across the weld bond interface;

measuring, subsequent to the application of the welding energy to the weld, the time required for the monitored emf to change from a first predetermined value of emf representative of a first predetermined weld temperature at which recrystallization of the weld has essentially begun to a second predetermined value of emf representative of a second predetermined weld temperature at which recrystallization of the weld is essentially complete, the measured time being representative of the weld mass of the metals;

comparing the measured time required for the emf to change from the first to the second predeermined values of emf with a predetermined time which is equal to the time required for a predetermined weld mass of metal to cool from the first to the second predetermined temperatures;

detecting the occurrence of a loss of the monitored emf, and generating an indication of a detected loss of the monitored emf.

5. In an apparatus for detecting the occurrence of a crack through a weld formed between two dissimilar metals by the application of welding energy to the weld, where an emf is generated across the weld bond interface and has a value directly related to the temperature of the weld interface as a result of the Seebeck effect:

means for monitoring the emf across the weld as a result of the emf generated across the weld bond interface;

means for detecting when the monitored emf ceases to increase in a first direction as the weld is heated upon the application of the welding energy thereto, and increases in a second and opposite direction as the weld cools subsequent to the application of the welding energy thereto;

detector circuitry, operative upon the monitored emf increasing in the second direction as the weld begins to cool for detecting the occurrence of a loss of the monitored emf, and an indicator for generating an output upon a detected loss of the monitored emf.

6. In an apparatus for testing a weld formed between two dissimilar metals by the application of welding energy to the weld, where an emf is generated across the weld bond interface as a result of the Seebeck effect and has a value directly related to the temperature of the weld interface:

means for detecting and for amplifying the emf across the weld as a result of the emf generated across the weld bond interface;

means for detecting, subsequent to the application of the welding energy to the weld, the rate of change of the emf across the weld with respect to time as the emf changes from a first predetermined value of emf representative of a weld temperature at which recrystallization of the weld has essentially begun to a second predetermined value of emf representative of a weld temperature at which recrystallization of the weld is essentially complete;

means for comparing the detected rate of change of emf with respect to time with a predetermined rate of emf change with respect to time which is indicative of a predetermined weld mass of the metals, and means for detecting, subsequent to the application of the welding energy to the weld, the occurrence of a loss of the detected emf.

* * * * *